(12) United States Patent
Chen et al.

(10) Patent No.: US 9,656,073 B2
(45) Date of Patent: May 23, 2017

(54) EXTERNAL ELECTRONIC EAR DEVICE AND COCHLEAR IMPLANT DEVICE

(71) Applicants: Kuang-Chao Chen, New Taipei (TW); SILICON MOTION, INC., Jhubei, Hsinchu (TW)

(72) Inventors: Kuang-Chao Chen, New Taipei (TW); Kuo-Liang Yeh, Hsinchu (TW)

(73) Assignees: KUANG-CHAO CHEN, New Taipei (TW); SILICON MOTION, INC., Jhubei, Hsinchu (TW)

( * ) Notice: Subject to any disclaimer, the term of this patent is extended or adjusted under 35 U.S.C. 154(b) by 0 days.

(21) Appl. No.: 14/996,239

(22) Filed: Jan. 15, 2016

(65) Prior Publication Data

US 2016/0206878 A1    Jul. 21, 2016

(30) Foreign Application Priority Data

Jan. 16, 2015    (TW) .............................. 104101524 A

(51) Int. Cl.
| | |
|---|---|
| *A61N 1/00* | (2006.01) |
| *A61N 1/36* | (2006.01) |
| *A61N 1/372* | (2006.01) |
| *A61N 1/375* | (2006.01) |
| *A61N 1/05* | (2006.01) |

(52) U.S. Cl.
CPC ......... *A61N 1/36032* (2013.01); *A61N 1/375* (2013.01); *A61N 1/37229* (2013.01); *A61N 1/0541* (2013.01)

(58) Field of Classification Search
CPC ..... A61N 1/36032; A61N 1/0541; A61N 1/37
See application file for complete search history.

(56) References Cited

U.S. PATENT DOCUMENTS

| | | | | |
|---|---|---|---|---|
| 6,402,782 | B1* | 6/2002 | Sibbald | A61B 17/0469 606/153 |
| 2008/0177353 | A1* | 7/2008 | Hirota | A61N 1/36032 607/57 |
| 2009/0082835 | A1* | 3/2009 | Jaax | H02J 7/025 607/61 |

(Continued)

FOREIGN PATENT DOCUMENTS

| | | |
|---|---|---|
| CN | 101360471 | 7/2010 |
| CN | 102600011 | 7/2012 |

*Primary Examiner* — Robert N Wieland
(74) *Attorney, Agent, or Firm* — Chieh-Mei Wang

(57) ABSTRACT

An external electronic ear device includes a housing, an external magnet, a microphone, a processing circuit and a wireless signal transmitter circuit. The external magnet is disposed in the housing and attracts a receiver magnet disposed under a scalp of a user. The microphone is disposed in the housing and receives an external sound and generates a sound signal corresponding to the external sound. The processing circuit is disposed in the housing and converts the sound signal into an electrode driving signal. The wireless signal transmitter circuit is disposed in the housing and transmits the electrode driving signal to a cochlear implant device in the cochlear system. The cochlear implant device converts the electrode driving signal into a plurality of electrode currents, and a plurality of electrical pulses are generated in a cochlear nerve of the user through a plurality of electrodes according to the electrode currents.

15 Claims, 5 Drawing Sheets

(56) References Cited

U.S. PATENT DOCUMENTS

| | | | |
|---|---|---|---|
| 2010/0292759 A1* | 11/2010 | Hahn | A61N 1/375 607/57 |
| 2011/0009924 A1* | 1/2011 | Meskens | A61N 1/36032 607/57 |
| 2013/0282070 A1* | 10/2013 | Cowan | A61N 1/326 607/3 |
| 2015/0110319 A1* | 4/2015 | Mimbs | H04R 25/02 381/322 |
| 2015/0164361 A1* | 6/2015 | Lunner | A61B 5/6817 600/379 |

* cited by examiner

EXTERNAL ELECTRONIC EAR DEVICE AND COCHLEAR IMPLANT DEVICE

FIELD OF THE INVENTION

The present invention relates to an external electronic ear device and a cochlear implant device, and more particularly to an external electronic ear device and a cochlear implant device for a user with hearing loss.

BACKGROUND OF THE INVENTION

Many people in the world are born with hearing loss. For a child born without hearing, he or she may never be able to talk. Therefore, providing auditory reconstruction to people with hearing loss is highly meaningful.

Please refer to FIG. 1, which is a schematic diagram of a conventional cochlear system. As shown in FIG. 1, the conventional cochlear system includes an external electronic ear device and a corresponding cochlear implant device. The external electronic ear device includes an external magnet 102, a processing circuit 103 and a microphone 105, which are worn by an ear 109 of a user. The external magnet 102 corresponds to a receiver magnet 104 of the cochlear implant device. The cochlear implant device further includes a stripe carrier body. The stripe carrier body is disposed in a cochlea 107 and for carrying a plurality of electrodes 106. The electrodes 106 are used to stimulate the auditory nerve to generate the nerve auditory signal, so that the user can have hearing when the nerve auditory signal is transmitted to the brain through the nerves system 108.

As the external magnet 102 and the processing circuit 103 are two separate components, the conventional external electronic ear device is typically large in size and can be conspicuous. In addition, since the external magnet 102, the processing circuit 103 and the microphone 105 are connected by wires, a user may feel uncomfortable while wearing the conventional external electronic ear device. Thus, there is an urgent need to develop an improved cochlear system.

SUMMARY OF THE INVENTION

The present invention provides an external electronic ear device in a cochlear system. The external electronic ear device includes a housing, an external magnet, a microphone, a processing circuit and a wireless signal transmitter circuit. The external magnet is disposed in the housing and configured to attract a receiver magnet disposed under a scalp of a user. The microphone is disposed in the housing and configured to receive an external sound and generate a sound signal corresponding to the external sound. The processing circuit is disposed in the housing and configured to convert the sound signal into an electrode driving signal. The wireless signal transmitter circuit is disposed in the housing and configured to transmit the electrode driving signal to a cochlear implant device in the cochlear system. The cochlear implant device is configured to convert the electrode driving signal into a plurality of electrode currents, and a plurality of electrical pulses are generated in a cochlear nerve of the user through a plurality of electrodes according to the electrode currents.

In one embodiment, the housing has a shell shape and the shell shape is customized and designed based on a head of the user, so that the housing and the head of the user substantially have a substantially similar color and a substantially similar shape.

In one embodiment, the housing is attached to a wig.

In one embodiment, the housing has a one-piece structure and is not connected to any component through wires.

In one embodiment, the wireless signal transmitter circuit includes a signal conversion circuit and a signal coil. The signal conversion circuit is configured to convert the electrode driving signal into a wireless communication format. The signal coil is configured to electromagnetically induce a signal coil in the cochlear implant device. The electrode driving signal having the wireless communication format is transmitted from the signal coil in the wireless signal transmitter circuit to the signal coil in the cochlear implant device through electromagnetic induction.

In one embodiment, the processing circuit is further configured to transmit a setting signal to the cochlear implant device according to a setting command, and the cochlear implant device adjusts the electrical pulses according to the setting signal.

In one embodiment, the cochlear implant device is configured to automatically detect an operation state thereof and generate a state signal accordingly. The state signal is then transmitted to the processing circuit, and the processing circuit is further configured to adjust the electrode driving signal according to the state signal.

In one embodiment, the aforementioned external electronic ear device further includes an external processor transmission interface. The processing circuit is further configured to transmit a to-be-processed sound signal corresponding to the external sound to an external processor through the external processor transmission interface. When the to-be-processed sound signal is processed by the external processor, a processing result is transmitted from the external processor to the processing circuit.

In one embodiment, the external processor transmission interface utilizes a short-range wireless communication protocol.

In one embodiment, the external processor transmission interface utilizes a Bluetooth protocol and the external processor is a mobile phone.

The present invention further provides a cochlear implant device in a cochlear system. The cochlear implant device includes a receiver magnet, a wireless signal receiver circuit, an electrode signal generator circuit and a plurality of electrodes. The receiver magnet is disposed under a scalp of a user and configured to attract an external magnet in an external electronic ear device in the cochlear system. The wireless signal receiver circuit is configured to receive an electrode driving signal from the external electronic ear device, wherein the electrode driving signal corresponds to an external sound. The electrode signal generator circuit is configured to convert the electrode driving signal into a plurality of electrode currents. The plurality of electrodes are configured to generate a plurality of electrical pulses in a cochlear nerve of a user according to the electrode currents, so that the user can have a hearing corresponding to the external sound. The wireless signal receiver circuit is further configured to transmit a state signal to the external electronic ear device according to an operation state of the cochlear implant device, and the external electronic ear device is configured to adjust the electrode driving signal according to the state signal.

In one embodiment, the aforementioned cochlear implant device further includes a module for disposing the wireless signal receiver circuit and the electrode signal generator circuit. The module is disposed in an ear canal of the user.

In one embodiment, the electrodes are disposed on a stripe carrier body, and the module and the stripe carrier body are electrically and physically connected to each other.

In one embodiment, the module and the stripe carrier body are connected to each other through a magnet force.

The present invention still further provides an external electronic ear device adapted to be used with a cochlear implant device. The external electronic ear device and the cochlear implant device cooperatively providing a user with a hearing. The external electronic ear device includes a housing, a microphone, a processing circuit and wireless signal transmitter circuit. The housing has a accommodating space. The housing is designed to have a shape based on the shape of an ear of the user, so that visually the housing is formed integrally with the ear of the user. The microphone is disposed in the accommodating space of the housing and configured to receive an external sound and generate a sound signal corresponding to the external sound. The processing circuit is disposed in the accommodating space of the housing and configured to convert the sound signal into an electrode driving signal. The wireless signal transmitter circuit is disposed in the accommodating space of the housing and configured to transmit the electrode driving signal to the cochlear implant device. The cochlear implant device is configured to convert the electrode driving signal into a plurality of electrode currents, and a plurality of electrical pulses are generated in a cochlear nerve of the user through a plurality of electrodes according to the electrode currents.

In one embodiment, the housing wraps around the ear of the user.

BRIEF DESCRIPTION OF THE DRAWINGS

Other advantages, objectives and features of the present invention will become apparent from the following description referring to the attached drawings.

DETAILED DESCRIPTION OF PREFERRED EMBODIMENTS

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1:
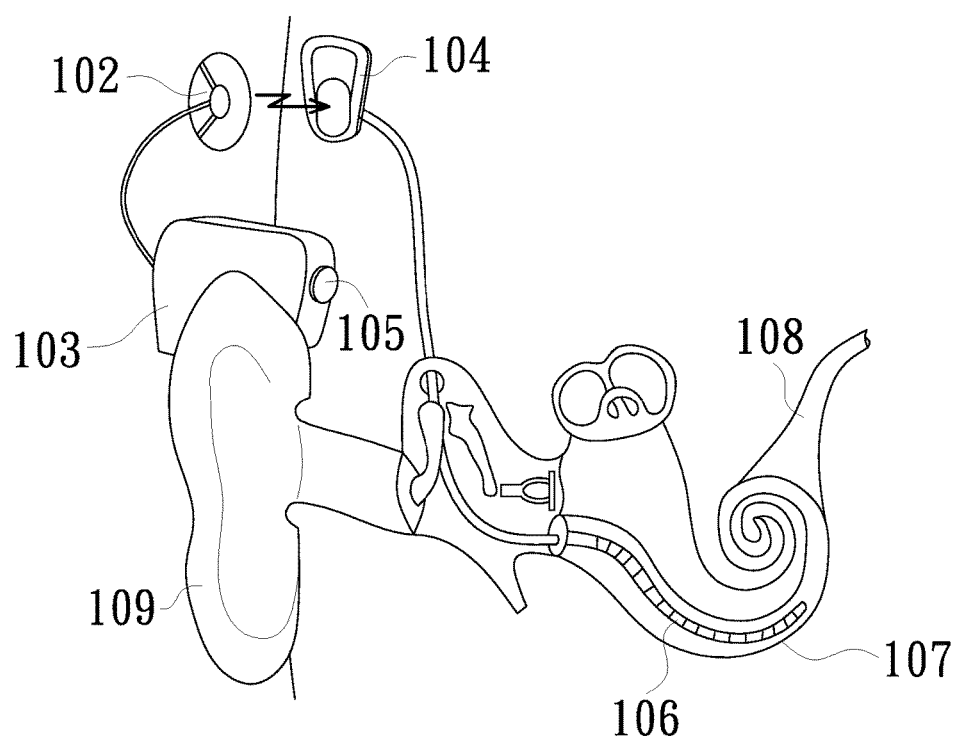
FIG. 1 is a is a schematic diagram of a conventional cochlear system.
Figure 2:
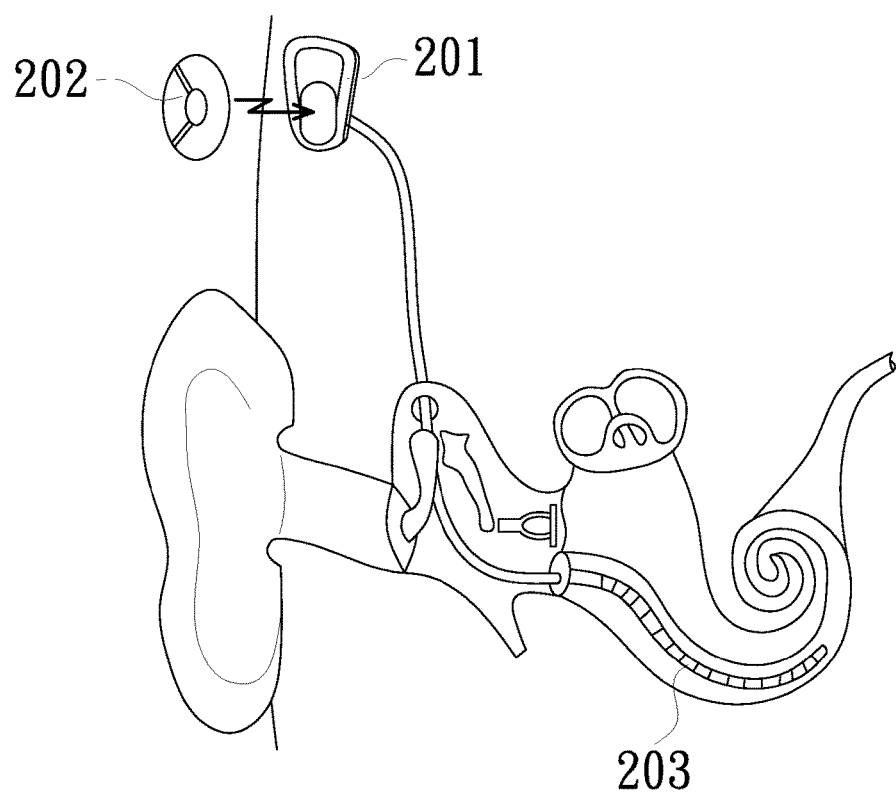
FIG. 2 is a schematic diagram of a cochlear system in accordance with an embodiment of the present invention.

Please refer to FIG. 2, which is a schematic diagram of a cochlear system in accordance with an embodiment of the present invention. As shown in FIG. 2, the cochlear system in the present embodiment includes an external electronic ear device and a corresponding cochlear implant device. The external electronic ear device includes a processing circuit (not shown), a microphone (not shown), an external magnet (not shown) and a wireless signal transmitter circuit (not shown). The processing circuit, the microphone, the external magnet and the wireless signal transmitter circuit are disposed in a housing 202. The cochlear implant device includes a receiver magnet 201 and a plurality of electrodes 203. The receiver magnet 201 in the cochlear implant device is used for attracting the external magnet in the external electronic ear device so as to secure the external electronic ear device at a predetermined position.

In one embodiment, the housing 202 may have a one-piece structure with circular, square, polygonal or other specific shapes, and is not connected to any component through wires. In addition, all of the aforementioned processing circuit, the microphone, the external magnet and the wireless signal transmitter circuit are disposed at respective predetermined positions in the housing 202. The housing 202 may be customized based on the shape or color of a user's head. The housing 202 is formed with an accommodating space, in which the aforementioned processing circuit, the microphone, the external magnet and the wireless signal transmitter circuit are disposed. In another embodiment, the housing 202 may be further provided with a wig, which is disposed on the external surface of the housing 202 and is designed with a specific color similar to that of the user's hair; thus, the user may involve in social activities more naturally without looking different.

Specifically, the external magnet is disposed at a predetermined position in the housing 202 and is configured to attract the receiver magnet 201 disposed under a user's scalp; thus, the housing 202 can be secured onto the external surface of the user's scalp. The microphone is disposed at a predetermined position in the housing 202 and is configured to receive an external sound and generate a sound signal. The microphone may be a directional or non-directional radio apparatus and capable of converting the external sound into a sound signal with electronic format. In one embodiment, the microphone herein is referred to as one signal microphone device. In another embodiment, the microphone herein is referred to as a combination of a plurality of microphone devices. The processing circuit is disposed at a predetermined position in the housing 202 and is configured to convert the sound signal from the microphone into an electrode driving signal. The processing circuit may be a microcontroller or an application specific integrated circuit (ASIC). In addition, the processing circuit may be implemented with a hardware logic circuit or a part of hardware circuit and a part of corresponding software logic.

In one embodiment, the processing circuit is further configured to transmit a setting signal to the cochlear implant device according to a setting command, so that the cochlear implant device can adjust a plurality of electrical pulses according to the setting signal. For example, a predetermined sound is provided to the user and the user can response to the quality of the predetermined sound. In one embodiment, the cochlear implant device can be set or adjusted properly according to the auditory responses, consequently providing more suitable electrical pulses. In another embodiment, the processing circuit may adjust the electrode driving signal according to the auditory responses so that the cochlear implant device can generate more suitable electrical pulses.

In one embodiment, the processing circuit can be operated in two modes. In one mode, when an external processor is detected, the sound signal is mainly processed by the detecting external processor. In another mode, when no external processor is detected, the sound signal is mainly processed by the processing circuit. In one embodiment, the cochlear implant device may be further configured to automatically detect its operation state and generate a state signal accordingly. The state signal is then transmitted to the processing circuit, and the processing circuit can adjust the electrode driving signal according to the state signal.

The wireless signal transmitter circuit transmits the electrode driving signal to the cochlear implant device. The cochlear implant device converts the electrode driving signal into a plurality of electrode currents, and a plurality of electrical pulses are generated in a cochlear nerve of the user through a plurality of electrodes according to the electrode currents. Thus, the external electronic ear device and the cochlear implant device cooperatively provide the user with a hearing corresponding to the external sound. In one embodiment, the wireless signal transmitter circuit includes a signal conversion circuit and a signal coil. The signal conversion circuit is configured to convert the electrode driving signal into a wireless communication format. The signal coil is configured to electromagnetically induce the signal coil in the cochlear implant device. Thus, the electrode driving signal having the wireless communication format is transmitted from the signal coil in the wireless signal transmitter circuit to the signal coil in the cochlear implant device through electromagnetic induction.

In one embodiment, the external electronic ear device may further include an external processor transmission interface (not shown in FIG. 2). Correspondingly, the processing circuit is further configured to transmit a to-be-processed sound signal corresponding to the external sound to an external processor (not shown) through the external processor transmission interface. Once the to-be-processed sound signal is processed by the external processor, a processing result is transmitted from the external processor to the processing circuit, and the processing circuit can obtain the electrode driving signal according to the processing result. In one embodiment, the external processor transmission interface is Bluetooth, Zigbee or any other type of customized short-range wireless communication protocol. The external processor can be mobile phones, tablet computers or other types of electronic devices. Through utilizing the external processor, the signal processing capability (such as noise filtering) is enhanced, consequently providing the user better sound signals. In addition, since the complicated signal processing is performed by the external processor, the processing circuit of the external electronic ear device can be smaller in size and more power-efficient.

Figure 3:
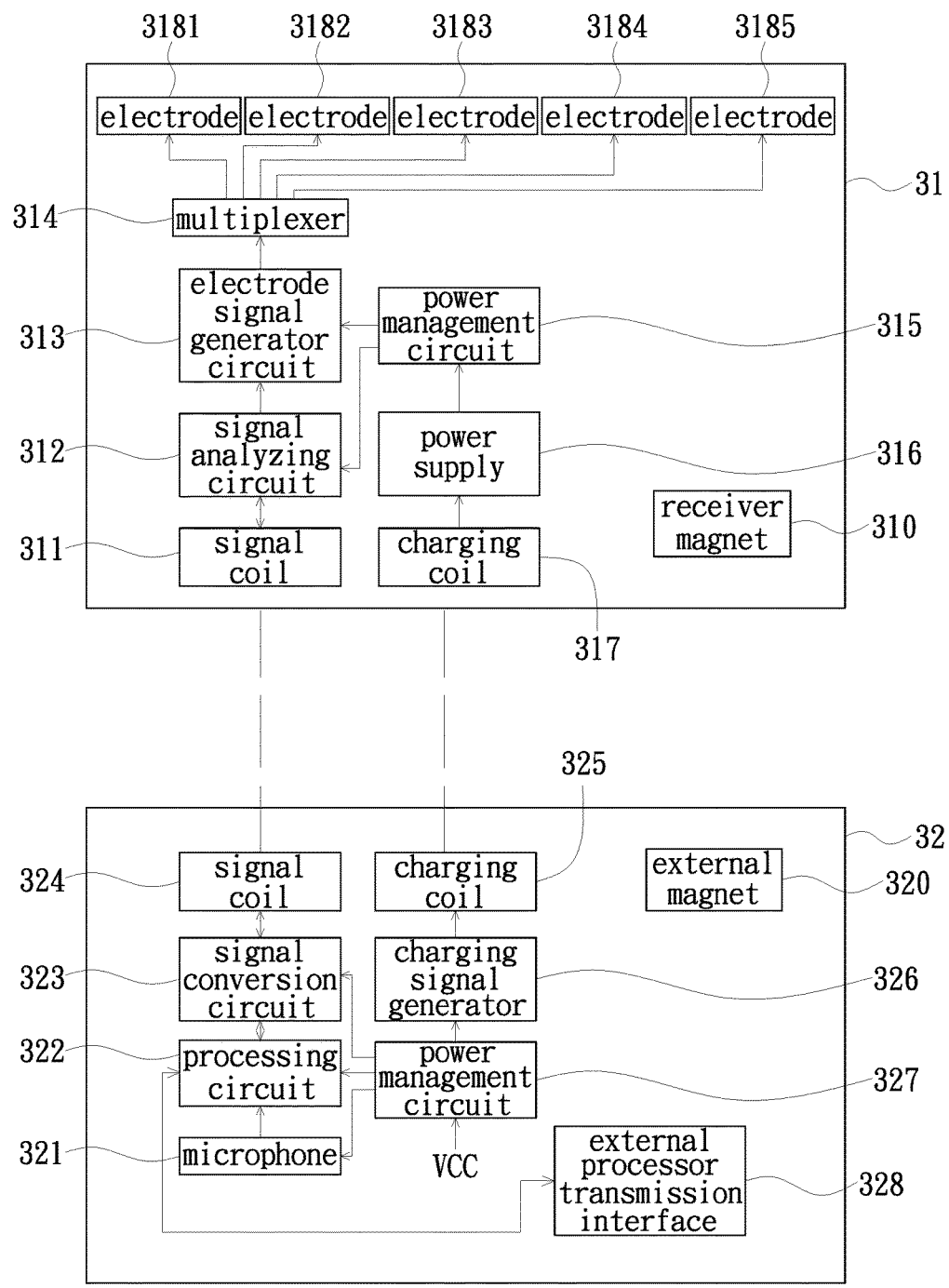
FIG. 3 is a circuit block diagram of a cochlear system in accordance with an embodiment of the present invention.

FIG. 3 is a circuit block diagram of a cochlear system in accordance with an embodiment of the present invention. As shown in FIG. 3, the cochlear system in the present embodiment includes a cochlear implant device 31 and an external electronic ear device 32. The external electronic ear device 32 includes an external magnet 320, a microphone 321, a processing circuit 322 and a wireless signal transmitter circuit; wherein the wireless signal transmitter circuit is comprised of a signal conversion circuit 323 and a signal coil 324. The configurations and functions of these aforementioned elements/devices have been described above, and no redundant detail is to be given herein. Preferably, the external electronic ear device 32 may further include a charging coil 325, a charging signal generator 326, a power management circuit 327 and an external processor transmission interface 328. The power management circuit 327 is electrically coupled to the microphone 321, the processing circuit 322 and the signal conversion circuit 323. In addition, the power management circuit 327 is further electrically coupled to the signal coil 324 through the charging signal generator 326. The power management circuit 327 is configured to convert a voltage level of a power supply voltage VCC (e.g., a voltage provided by a battery) into the respective voltage levels capable of being used by the microphone 321, the processing circuit 322 and the signal conversion circuit 323. Moreover, the power management circuit 327 is further configured to control the charging signal generator 326 to generate a charging signal, which is then transmitted to the cochlear implant device 31 through the charging coil 325. The external processor transmission interface 328 is electrically coupled to the processing circuit 322 and configured to have signal transmission with the processing circuit 322.

As shown in FIG. 3, the cochlear implant device 31 mainly includes a receiver magnet 310, a wireless signal receiver circuit, an electrode signal generator circuit 313, a multiplexer 314 and a plurality of electrodes (herein the electrodes 3181, 3182, 3183, 3184 and 3185 are exemplarily shown); wherein the wireless signal receiver circuit is comprised of a signal coil 311 and a signal analyzing circuit 312. The signal analyzing circuit 312 is configured to receive and analyze the electrode driving signal transmitted from the external electronic ear device 32 through the signal coil 311 and control the electrode signal generator circuit 313 to generate a plurality of electrode currents. Preferably, the cochlear implant device 31 may further include a power management circuit 315, a power supply 316 and a charging coil 317. The charging coil 317 is electrically coupled to the power management circuit 315 through the power supply 316 (e.g., a capacitor). The power management circuit 315 is electrically coupled to the signal analyzing circuit 312 and the electrode signal generator circuit 313. The charging coil 317 is configured to receive the charging signal from the charging coil 325 of the external electronic ear device 32 and charge the power supply 316 accordingly. The power management circuit 315 is configured to convert the voltage level of the electrical power stored in the power supply 316 into the respective voltage levels capable of being used by the signal analyzing circuit 312 and the electrode signal generator circuit 313.

In the external electronic ear device 32, the microphone 321 may be a directional or non-directional radio apparatus and capable of converting the external sound into a sound signal with electronic format. In one embodiment, the microphone 321 herein is referred to as one signal microphone device. In another embodiment, the microphone 321 herein is referred to as a combination of a plurality of microphone devices. The processing circuit 322 is configured to convert the sound signal from the microphone 321 into an electrode driving signal. The processing circuit 322 may be a microcontroller or an application specific integrated circuit (ASIC). In addition, the processing circuit 322 may be implemented with a hardware logic circuit or a part of hardware circuit and a part of corresponding software logic.

As described above, the microphone 321 converts the external sound into the sound signal. In one embodiment, the processing circuit 322 is further configured to filter and amplify the sound signal and then convert the processed sound signal into the corresponding electrode driving signal. The signal conversion circuit 323 is configured to convert the electrode driving signal into a signal with specific format capable of being transmitted in a wireless manner, and the signal with specific format is then transmitted to the signal coil 311 of the cochlear implant device 31 through the signal coil 324. Once the signal coil 311 receives the signal transmitted from the signal coil 324, the signal analyzing circuit 312 is configured to analyze the signal received by the signal coil 311. It is to be noted that the signal transmitted from the signal coil 324 to the signal coil 311 may be designed to have an analog format or a digital format and is corresponding to the respective sound signal in packet format. In one embodiment, the signal analyzing circuit 312 may further provide signal decompression, demodulation or decryption functions if the external electronic ear device 32 is provided with the signal compression, modulation or encryption functions.

The signal analyzed by the signal analyzing circuit 312 is then converted into a plurality of electrode currents by the electrode signal generator circuit 313. The multiplexer 314 is configured to transmit the electrode currents to the electrodes 3181, 3182, 3183, 3184 and 3185 through wires, respectively. Because these electrodes 3181, 3182, 3183, 3184 and 3185 are disposed at different positions in the cochlea and each position in the cochlea corresponds to a respective frequency, in general Fourier Transform is utilized for the time-frequency space conversion.

The power management circuit 327 of the external electronic ear device 32 is responsible for power management. Specifically, the power management circuit 327 is configured to control the charging signal generator 326 to generate the charging signal. The charging signal is then transmitted to the charging coil 317 of the cochlear implant device 31 from the charging coil 325; thus, the power supply 316 is charged by the charging signal through a control of the power management circuit 315.

In order to make the external electronic ear device less conspicuous, the housing of the external electronic ear device may be designed to have a shape similar to that of a user's ear. In one embodiment, the design of the housing of the external electronic ear device may be realized by utilizing laser scans to establish a three-dimensional model of the user's ear.

Figure 4:
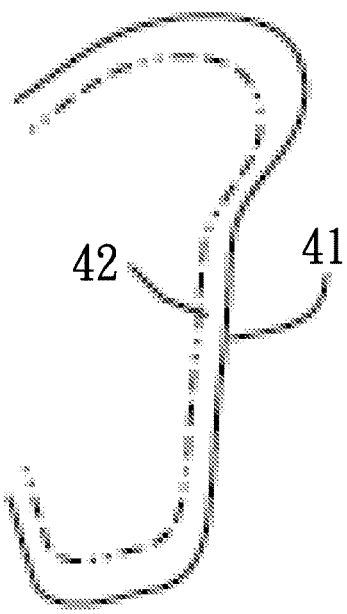
FIG. 4 is a schematic diagram of a housing of an external electronic ear device in accordance with an embodiment of the present invention.

FIG. 4 is a schematic diagram of a housing of an external electronic ear device in accordance with an embodiment of the present invention. As shown in FIG. 4, the housing 41 of the external electronic ear device in the present embodiment is designed to have a shape corresponding to the shape of a user's ear 42, so that the housing 41 is able to wrap around the user's ear 42. Moreover, by further designing the housing 41 of the external electronic ear device to have a color similar to that of the user's ear 42, the external electronic ear device would resemble a real ear of the user. In addition, by designing the housing 41 of the external electronic ear device to have a shape corresponding to the user's ear 42, the external electronic ear device can be secured onto the user's ear 42 without the external magnet, and magnetic resonance imaging (MRI) issues are avoided.

Figure 5:
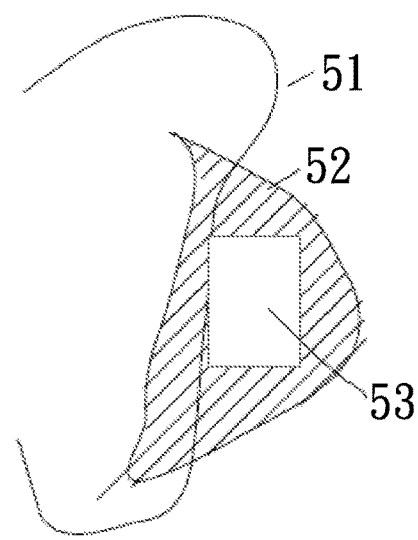
FIG. 5 is a schematic diagram of a housing of an external electronic ear device in accordance with another embodiment of the present invention.

FIG. 5 is a schematic diagram of a housing of an external electronic ear device in accordance with another embodiment of the present invention. As shown in FIG. 5, the housing 52 of the external electronic ear device in the present embodiment is designed to have a shape corresponding to a part of an ear 51 (specifically, the backside of the ear 51). In addition, the housing 52 is formed with an accommodating space 53. The accommodating space 53 is configured for disposing the processing circuit, the microphone and the related components. Thus, the processing circuit, the microphone and the related components can be manufactured in a standardized manner while the housing 51 can still have customized shape and color according to real ear of the user. In addition, by designing the module (comprised of the processing circuit, the microphone and the related components) capable of being easily engaged into the housing 52, the external electronic ear device has lower manufacturing cost and a user can wear the external electronic ear device more comfortably.

Because the housing 52 may be designed to have a shape based on the shape of the ear 51 of the user, visually the housing 52 is formed integrally with the ear 51 of the user and is less conspicuous. In addition, the housing 52 is provided with an accommodating space 53, in which the aforementioned microphone, processing circuit and wireless signal transmitter circuit are disposed. As described above, the microphone is for converting an external sound into a sound signal. The processing circuit is for converting the sound signal into an electrode driving signal. The wireless signal transmitter circuit is for transmitting the electrode driving signal to the cochlear implant device. The cochlear implant device converts the electrode driving signal into a plurality of electrode currents. Then, through a plurality of electrodes, a plurality of electrical pulses is generated in the cochlear nerve according to the electrode currents. Thus, the user can have a hearing corresponding to the external sound.

Thus, through the aforementioned design, the external electronic ear device may be designed to be less conspicuous, so that the user is more willing to wear the external electronic ear device and consequently can be more involved in social activities.

Figure 6:
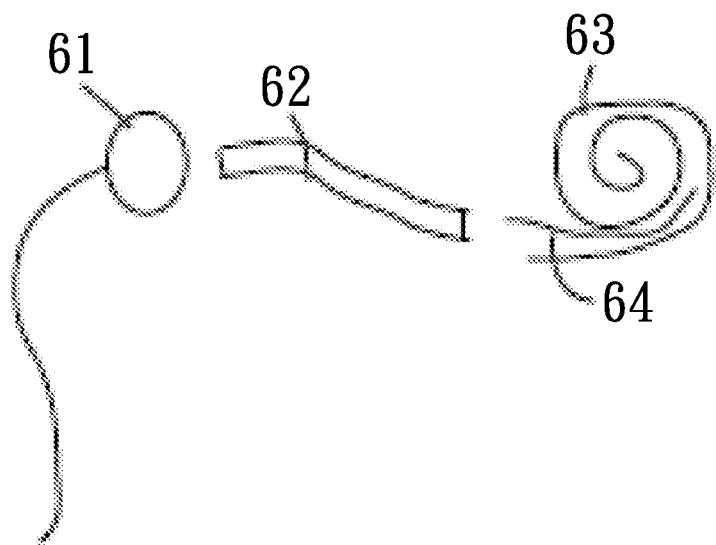
FIG. 6 is a schematic diagram of a cochlear system in accordance with another embodiment of the present invention.

FIG. 6 is a schematic diagram of a cochlear system in accordance with another embodiment of the present invention. In the present embodiment as shown in FIG. 6, the processing circuit, the microphone and the related components are integrated as a module 62 and disposed in a user's ear canal. The electrodes are disposed on a stripe carrier body 64, and the stripe carrier body 64 is placed in the user's cochlea 63. The module 62 and the stripe carrier body 64 may be electrically and physically connected to each other through magnets and may have wireless signal transmission with each other. The module 62 can be charged by a charger 61, which may be designed to have an earphone shape. Thus, the module 62 can have a smaller component size and the charger 61 can have a less-conspicuous shape, so that the user may involve in social activities more naturally without looking different.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. An external electronic ear device in a cochlear system, the external electronic ear device comprising:
   a housing;
   an external magnet, disposed in the housing and configured to attract a receiver magnet disposed under a scalp of a user;
   a microphone, disposed in the housing and configured to receive an external sound and generate a sound signal corresponding to the external sound;
   a processing circuit, disposed in the housing and configured to convert the sound signal into an electrode driving signal;

a wireless signal transmitter circuit, disposed in the housing and configured to transmit the electrode driving signal to a cochlear implant device in the cochlear system;

a power management circuit, disposed in the housing and configured to generate a plurality of respective voltage levels capable of being used by the microphone and the processing circuit; and a charging coil, disposed in the housing and configured to transmit a charging signal generated according to the power management circuit to the cochlear implant device for charging a power supply of the cochlear implant device, wherein the cochlear implant device is configured to convert the electrode driving signal into a plurality of electrode currents, and a plurality of electrical pulses are generated in a cochlear nerve of the user through a plurality of electrodes according to the electrode currents.

2. The external electronic ear device according to claim 1, wherein the housing has a shell shape and the shell shape is customized and designed based on a head of the user so that the housing and the head of the user have a substantially similar color and a substantially similar shape.

3. The external electronic ear device according to claim 2, wherein the housing is attached to a wig.

4. The external electronic ear device according to claim 1, wherein the housing has a one-piece structure and is not connected to any component through wires.

5. The external electronic ear device according to claim 1, wherein the wireless signal transmitter circuit comprises:

a signal conversion circuit, configured to convert the electrode driving signal into a wireless communication format; and a signal coil, configured to electromagnetically induce a signal coil in the cochlear implant device, wherein the electrode driving signal having the wireless communication format is transmitted from the signal coil in the wireless signal transmitter circuit to the signal coil in the cochlear implant device through electromagnetic induction.

6. The external electronic ear device according to claim 1, wherein the processing circuit is further configured to transmit a setting signal to the cochlear implant device according to a setting command, and the cochlear implant device adjusts the electrical pulses according to the setting signal.

7. The external electronic ear device according to claim 1, wherein the cochlear implant device is configured to automatically detect an operation state thereof and generate a state signal accordingly, the state signal is then transmitted to the processing circuit, and the processing circuit is further configured to adjust the electrode driving signal according to the state signal.

8. The external electronic ear device according to claim 1, further comprising an external processor transmission interface, wherein the processing circuit is further configured to transmit a to-be-processed sound signal corresponding to the external sound to an external processor through the external processor transmission interface, wherein when the to-be-processed sound signal is processed by the external processor, a processing result is transmitted from the external processor to the processing circuit.

9. The external electronic ear device according to claim 8, wherein the external processor transmission interface utilizes a short-range wireless communication protocol.

10. The external electronic ear device according to claim 8, wherein the external processor transmission interface utilizes a Bluetooth protocol and the external processor is a mobile phone.

11. A cochlear implant device in a cochlear system, the cochlear implant device comprising:

a receiver magnet, disposed under a scalp of a user and configured to attract an external magnet in an external electronic ear device in the cochlear system;

a wireless signal receiver circuit, configured to receive an electrode driving signal from the external electronic ear device, wherein the electrode driving signal corresponds to an external sound;

an electrode signal generator circuit, configured to convert the electrode driving signal into a plurality of electrode currents; and a plurality of electrodes, configured to generate a plurality of electrical pulses in a cochlear nerve of a user according to the electrode currents, so that the user can have a hearing corresponding to the external sound, wherein the module and the stripe carrier body are connected to each other through a magnet force, wherein the wireless signal receiver circuit is further configured to transmit a state signal to the external electronic ear device according to an operation state of the cochlear implant device, and the external electronic ear device is configured to adjust the electrode driving signal according to the state signal.

12. The cochlear implant device according to claim 11, wherein the cochlear implant device further comprises a module for disposing the wireless signal receiver circuit and the electrode signal generator circuit, the module is disposed in an ear canal of the user.

13. The cochlear implant device according to claim 12, wherein the electrodes are disposed on a stripe carrier body, and the module and the stripe carrier body are electrically and physically connected to each other.

14. An external electronic ear device adapted to be used with a cochlear implant device, the external electronic ear device and the cochlear implant device cooperatively providing a user with a hearing, the external electronic ear device comprising:

a housing, having an accommodating space, wherein the housing is designed to have a shape based on the shape of an ear of the user, so that visually the housing is formed integrally with the ear of the user;

a microphone, disposed in the accommodating space of the housing and configured to receive an external sound and generate a sound signal corresponding to the external sound;

a processing circuit, disposed in the accommodating space of the housing and configured to convert the sound signal into an electrode driving signal;

a wireless signal transmitter circuit, disposed in the accommodating space of the housing and configured to transmit the electrode driving signal to the cochlear implant device;

a power management circuit, disposed in the housing and configured to generate a plurality of respective voltage levels capable of being used by the microphone and the processing circuit; and a charging coil, disposed in the housing and configured to transmit a charging signal generated according to the power management circuit to the cochlear implant device for charging a power supply of the cochlear implant device, wherein the cochlear implant device is configured to convert the electrode driving signal into a plurality of electrode currents, and a plurality of electrical pulses are generated in a cochlear nerve of the user through a plurality of electrodes according to the electrode currents.

15. The external electronic ear device according to claim 14, wherein the housing wraps around the ear of the user.

* * * * *